US008357361B2

(12) United States Patent
Hadba et al.

(10) Patent No.: US 8,357,361 B2
(45) Date of Patent: *Jan. 22, 2013

(54) BIOABSORBABLE SURGICAL COMPOSITION

(75) Inventors: Ahmad R. Hadba, Wallingford, CT (US); Nadya Belcheva, Middletown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/948,087

(22) Filed: Nov. 17, 2010

(65) Prior Publication Data

US 2011/0059061 A1    Mar. 10, 2011

Related U.S. Application Data

(62) Division of application No. 11/635,365, filed on Dec. 6, 2006, now Pat. No. 7,858,078.

(60) Provisional application No. 60/742,708, filed on Dec. 6, 2005.

(51) Int. Cl.
*A61K 31/74* (2006.01)
*A61F 2/00* (2006.01)
*C08F 283/04* (2006.01)
*C08L 77/06* (2006.01)

(52) U.S. Cl. ............... 424/78.27; 424/423; 424/426; 525/438; 525/453

(58) Field of Classification Search .......... None
See application file for complete search history.

(56) References Cited

U.S. PATENT DOCUMENTS

| | | | |
|---|---|---|---|
| 3,631,138 A | 12/1971 | Peters | |
| 3,773,595 A | 11/1973 | Burba et al. | |
| 3,879,493 A | 4/1975 | Mudde | |
| 3,903,232 A | 9/1975 | Wood et al. | |
| 3,975,550 A | 8/1976 | Fioriti et al. | |
| 4,057,535 A | 11/1977 | Lipatova et al. | |
| 4,061,662 A | 12/1977 | Marans et al. | |
| 4,132,839 A | 1/1979 | Marans et al. | |
| 4,169,175 A | 9/1979 | Marans et al. | |
| 4,321,350 A | 3/1982 | Lehmann | |
| 4,323,491 A | 4/1982 | Veselovsky et al. | |
| 4,404,296 A | 9/1983 | Schapel | |
| 4,425,472 A | 1/1984 | Howard et al. | |
| 4,451,627 A | 5/1984 | Frisch, Jr. et al. | |
| 4,477,604 A | 10/1984 | Oechsle, III | |
| 4,511,626 A | 4/1985 | Schumacher | |
| 4,547,561 A | 10/1985 | Wegner | |
| 4,654,409 A | 3/1987 | Shirai et al. | |
| 4,681,934 A | 7/1987 | Shibanai et al. | |
| 4,722,815 A | 2/1988 | Shibanai | |
| 4,725,653 A | 2/1988 | Koleske | |
| 4,740,534 A | 4/1988 | Matsuda et al. | |
| 4,743,632 A | 5/1988 | Marinovic | |
| 4,762,899 A | 8/1988 | Shikinami | |
| 4,804,691 A | 2/1989 | English et al. | |
| 4,806,614 A | 2/1989 | Matsuda et al. |
| 4,829,099 A | 5/1989 | Fuller et al. |
| 4,883,837 A | 11/1989 | Zabrocki |
| 4,994,208 A | 2/1991 | McBain et al. |
| 4,994,542 A | 2/1991 | Matsuda et al. |
| 4,997,656 A | 3/1991 | Shikinami et al. |
| 5,065,752 A | 11/1991 | Sessions et al. |
| 5,082,663 A | 1/1992 | Konishi et al. |
| 5,166,300 A | 11/1992 | Rumon et al. |
| 5,169,720 A | 12/1992 | Braatz et al. |
| 5,173,301 A | 12/1992 | Itoh et al. |
| 5,175,228 A | 12/1992 | Wang et al. |
| 5,204,110 A | 4/1993 | Cartmell et al. |
| 5,346,981 A | 9/1994 | Sarpeshkar et al. |
| 5,374,704 A | 12/1994 | Muller et al. |
| 5,389,718 A | 2/1995 | Potter et al. |
| 5,457,141 A | 10/1995 | Matsuda |
| 5,462,536 A | 10/1995 | Braatz et al. |
| 5,574,104 A | 11/1996 | Kolycheck et al. |
| 5,574,123 A | 11/1996 | Bock et al. |
| 5,578,662 A | 11/1996 | Bennett et al. |
| 5,603,798 A | 2/1997 | Bhat |
| 5,672,652 A | 9/1997 | Bhat |
| 5,688,860 A | 11/1997 | Croft |
| 5,702,717 A | 12/1997 | Cha et al. |
| 5,703,158 A | 12/1997 | Duan et al. |
| 5,711,958 A | 1/1998 | Cohn et al. |
| 5,717,030 A | 2/1998 | Dunn et al. |
| 5,780,573 A | 7/1998 | Iwata et al. |
| 5,791,352 A | 8/1998 | Reich et al. |
| 5,795,633 A | 8/1998 | Yokoyama et al. |
| 5,869,566 A | 2/1999 | Thomas |
| 5,900,473 A | 5/1999 | Acevedo et al. |
| 5,912,193 A | 6/1999 | Iwata et al. |
| 5,922,809 A | 7/1999 | Bhat et al. |
| 5,948,427 A | 9/1999 | Yamamoto et al. |
| 5,976,305 A | 11/1999 | Bhat et al. |

(Continued)

FOREIGN PATENT DOCUMENTS

EP    0 077 192 A2    4/1983
EP    0 482 467 A2    4/1992

(Continued)

OTHER PUBLICATIONS

European Search Report (EP 06 00 9170), dated Aug. 24, 2006.
Margolin A L et al.: "Steroselective Oligomerizations Catalyzed by Lipases in Organic Olvents"; Tetrahedron Letters, vol. 28, No. 15, 1987 pp. 1607-1610.
Okumura S. et al.: "Synthesis of Ester Oligomer by AspergillNiger Lipase" Agricultural and Biological Chemistry, vol. 48, No. 11, 1984, pp. 2805-2808.
Lumann N R et al.: The convergent Synthesis of Poly(glycerol-succininc acid) Dendritic Marcomolecules: Chemistry—A European Journal, VCH Publishers, US vol. 9, 2003, pp. 5618-5626.
Database WPI, Section Ch, Week 199442 Derwent Publications Ltd. London, GB; AN 1994-3383493.

(Continued)

*Primary Examiner* — Robert A Wax
*Assistant Examiner* — Jeffrey T Palenik

(57) ABSTRACT

Bioabsorbable macromer compositions are provided including a diisocyanate-functional bioabsorbable polymer. In some embodiments, the diisocyanate-functional bioabsorbable polymer can be combined with a functionalized polyol. The resulting bioabsorbable macromer composition can be employed as an adhesive or sealant for medical/surgical uses.

13 Claims, No Drawings

U.S. PATENT DOCUMENTS

| | | | |
|---|---|---|---|
| 5,990,237 | A | 11/1999 | Bentley et al. |
| 6,071,530 | A | 6/2000 | Polson et al. |
| 6,103,850 | A | 8/2000 | Reichel et al. |
| 6,154,089 | A | 11/2000 | Rombach |
| 6,162,241 | A | 12/2000 | Coury et al. |
| 6,197,915 | B1 | 3/2001 | Yamana et al. |
| 6,217,894 | B1 | 4/2001 | Sawhney et al. |
| 6,235,815 | B1 | 5/2001 | Loercks et al. |
| 6,261,544 | B1 | 7/2001 | Coury et al. |
| 6,290,729 | B1 | 9/2001 | Sleplan et al. |
| 6,296,908 | B1 | 10/2001 | Reihs et al. |
| 6,297,349 | B1 | 10/2001 | Goldberg et al. |
| 6,312,725 | B1 | 11/2001 | Wallace et al. |
| 6,339,130 | B1 | 1/2002 | Bennett et al. |
| 6,352,710 | B2 | 3/2002 | Sawhney et al. |
| 6,395,112 | B1 | 5/2002 | Sitzmann et al. |
| 6,395,823 | B1 | 5/2002 | Brink et al. |
| 6,461,631 | B1 | 10/2002 | Dunn et al. |
| 6,465,001 | B1 | 10/2002 | Hubbell et al. |
| 6,465,004 | B1 | 10/2002 | Rossi-Montero et al. |
| 6,495,127 | B1 | 12/2002 | Wallace et al. |
| 6,512,033 | B1 | 1/2003 | Wu |
| 6,555,645 | B1 | 4/2003 | Ikeda et al. |
| 6,565,969 | B1 | 5/2003 | Lamon et al. |
| 6,576,702 | B2 | 6/2003 | Anderle et al. |
| 6,579,952 | B1 | 6/2003 | Niki et al. |
| 6,582,713 | B2 | 6/2003 | Newell et al. |
| 6,605,666 | B1 | 8/2003 | Scholz et al. |
| 6,824,703 | B2 | 11/2004 | Lawrey et al. |
| 7,858,078 | B2 * | 12/2010 | Hadba et al. ............... 424/78.27 |
| 2002/0028875 | A1 | 3/2002 | Anderle et al. |
| 2003/0032734 | A1 | 2/2003 | Roby |
| 2003/0035786 | A1 | 2/2003 | Hendriks et al. |
| 2003/0044380 | A1 | 3/2003 | Zhu et al. |
| 2003/0176615 | A1 | 9/2003 | Lawrey et al. |
| 2003/0195293 | A1 | 10/2003 | Lubnin et al. |
| 2004/0019178 | A1 | 1/2004 | Gross et al. |
| 2004/0023842 | A1 | 2/2004 | Pathak et al. |
| 2004/0068078 | A1 | 4/2004 | Milbocker |
| 2004/0092695 | A1 | 5/2004 | Hu et al. |
| 2004/0198901 | A1 | 10/2004 | Graham et al. |
| 2004/0198944 | A1 | 10/2004 | Meltzer |
| 2004/0242831 | A1 | 12/2004 | Tian et al. |
| 2004/0259968 | A1 | 12/2004 | Krebs |
| 2005/0004661 | A1 | 1/2005 | Lewis et al. |
| 2005/0069573 | A1 | 3/2005 | Cohn et al. |
| 2005/0070913 | A1 | 3/2005 | Milbocker et al. |
| 2005/0129733 | A1 | 6/2005 | Milbocker et al. |
| 2005/0131192 | A1 | 6/2005 | Matsuda et al. |
| 2005/0142162 | A1 | 6/2005 | Hunter et al. |
| 2005/0147647 | A1 | 7/2005 | Glauser et al. |
| 2005/0154148 | A1 | 7/2005 | Nakamichi et al. |
| 2005/0266086 | A1 | 12/2005 | Sawhney |
| 2006/0253094 | A1 | 11/2006 | Hadba et al. |
| 2007/0128152 | A1 | 6/2007 | Hadba et al. |
| 2007/0135605 | A1 | 6/2007 | Hadba et al. |
| 2007/0135606 | A1 | 6/2007 | Belcheva et al. |

FOREIGN PATENT DOCUMENTS

| | | |
|---|---|---|
| EP | 0 488 629 A1 | 6/1992 |
| EP | 0 301 516 B1 | 9/1992 |
| EP | 1 391 205 A1 | 2/2005 |
| EP | 1 719 530 A | 11/2005 |
| EP | 1 719 530 A2 | 11/2006 |
| GB | 985 144 | 3/1965 |
| GB | 1 143 309 | 2/1969 |
| GB | 1 187 362 | 4/1970 |
| JP | 6263850 | 9/1994 |
| JP | 2002060341 | 2/2002 |
| WO | WO 89/00589 A1 | 1/1989 |
| WO | WO 00/43050 A1 | 7/2000 |
| WO | WO 01/00246 A | 1/2001 |
| WO | WO 01/16210 A | 3/2001 |
| WO | WO 03/011173 A2 | 2/2003 |
| WO | WO 03/011173 A3 | 2/2003 |
| WO | WO 2004/039323 A2 | 5/2004 |
| WO | WO 2004/039323 A3 | 5/2004 |
| WO | WO 2004/039857 A1 | 5/2004 |
| WO | WO 2004/041890 A1 | 5/2004 |
| WO | WO 2005/100429 A1 | 10/2005 |
| WO | WO 2006/010278 A1 | 2/2006 |
| WO | WO 2007/067623 A | 6/2007 |
| WO | WO 2008/047100 A1 | 4/2008 |

OTHER PUBLICATIONS

Nivasu V M et al.: "In Situ Polymerizable Polyethyleneglycol Containing Polyesterpolyol Acrylates for Tissue Sealant Applications"; Biomaterials 2004 United Kingdom, vol. 25, No. 16, 2004 pp. 3283-3291.

Moon S-Y et al.: Polyurethane/Montorillonite Nancomposites Prepared From Crystalline Polyols, Using 1, 4-Butanediol and Organoclay Hybrids as Chain Extenders: European Polymer Journal, Pergamon Press Ltd. Oxford, GB,; vol. 40, No. 8, Aug. 2004; pp. 1615-16213.

M. J. Song, et al.: "Thermosensitive Sol-Gel Transition Behaviors of Poly(ethylene oide)/ Aliphatic Polyester/Poly(ethylene Oxide) Aqueous Solutions"; Journal of Polymer Science Part A: Polymer Chemistry, vol. 42, No. 3.; Feb. 1, 2004; pp. 772-784.

Mei Xuan Xu et al.: Synthesis and Properties of Unsaturated Polyester Dio-Polyurethanehybrid Polymer Network: Journal of Applied Polymer Science, John Wiley and Sons Inc. New York, US, vol. 54, No. 11, Dec. 12, 1994, pp. 1659-1663.

Oprea S. et a!.: "Poly(urethane-methacrylates)s. Synthesis and Characterization"; Polymer, Elsevier Science Publishers B.V., GB, vol. 42, No. 17, Aug. 2001, pp. 7257-7266.

Ferreira, et al., "Modification of the Biopolymer Castor Oil With Free Isocyanate Groups to Be Applied As Bioadhesive", *International Journal of Biological Macromolecules*, vol., 40, No. 2, pp. 144-152 (2007).

Ferreira, et al., "Development of a Biodegradable Bioadhesive Containing Urethane Groups", *Journal of Materials Science: Materials in Medicine*, vol. 19, No. 1, pp. 111-120 (2007).

International Search Report from European Application No. EP 08 25 3645 mailed Mar. 5, 2009.

International Search Report (PCT/US2006/46558 dated Nov. 9, 2007).

European Search Report for Appln. No. EP 08 25 3647 completed Mar. 6, 2009.

European Search Report for Appln. No. EP 08 25 1790.5 completed Jun. 19, 2009.

International Search Report from Application No. PCT/US08/60971 dated Jul. 18, 2008.

International Search Report from Application No. PCT/US06/47013 dated Oct. 3, 2007.

International Search Report from Application No. PCT/US06/46558 dated Nov. 9, 2007.

International Search Report from Application No. PCT/US06/46552 dated Nov. 15, 2007.

International Search Report from Application No. PCT/US06/47023 dated Nov. 21, 2007.

International Search Report from Application No. EP 07 00 1213 dated Sep. 6, 2007.

International Search Report from Application No. EP 03 77 9244 dated Sep. 26, 2007.

International Search Report from Application No. PCT/US2006/46553 dated Oct. 31, 2007.

Supplementary European Search Report from Application No. EP 06 84 4894 dated Jun. 23, 2010 (8 pages).

A Supplementary European Search Report from Application No. EP 06839253.9-2115 dated Jul. 16, 2012.

* cited by examiner

BIOABSORBABLE SURGICAL COMPOSITION

CROSS-REFERENCE TO RELATED APPLICATIONS

This application is a divisional application of U.S. patent application Ser. No. 11/635,365, filed on Dec. 6, 2006, now U.S. Pat. No. 7,858,078 issued Dec. 28, 2010 which, in turn, claims the benefit of and priority to U.S. Provisional Patent Application No. 60/742,708 filed Dec. 6, 2005, the entire disclosures of each of which are incorporated by reference herein.

TECHNICAL FIELD

The present disclosure relates to bioabsorbable macromers capable of forming a matrix and the use of these macromers as surgical adhesives or sealants.

DESCRIPTION OF THE RELATED ART

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, there is the possibility that a cyanoacrylate adhesive can degrade to generate undesirable by-products such as formaldehyde. Another disadvantage with cyanoacrylate adhesives is that they can have a high flexural modulus which can limit their usefulness.

Another type of tissue sealant that is currently available utilizes components derived from bovine and/or human sources. For example, fibrin sealants are available. However, as with any natural material, variability in the material is frequently observed and, because the sealant is derived from natural proteins, there may be viral transmission concerns.

It would be desirable to provide a biological adhesive that is fully synthetic and therefore highly consistent in its properties without the concern of viral transmission. Such a composition should be flexible and biocompatible and should be suitable for use as an adhesive or sealant.

SUMMARY

The present disclosure is directed to bioabsorbable macromer compositions which include a diisocyanate-functional bioabsorbable polymer optionally in combination with at least one functionalized polyol. In embodiments the bioabsorbable polymer is a polyalkylene oxide which contains bioabsorbable groups.

In embodiments, the bioabsorbable macromer composition of the present disclosure may include a diisocyanate-functional bioabsorbable polymer of the general formula:

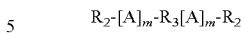

wherein A is a bioabsorbable group such as lactide, glycolide, ε-caprolactone, trimethylene carbonate, p-dioxanone, anhydrides, phosphoesters, and combinations thereof, $R_3$ is a polyethylene glycol, $R_2$ is an isocyanate group, and m is a number from about 1 to about 6.

In other embodiments, a bioabsorbable macromer composition of the present disclosure may include a diisocyanate-functional bioabsorbable polymer of the general formula:

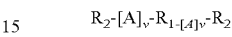

wherein $R_1$ is a polymer such as polysaccharides and polyols, A is a bioabsorbable group, $R_2$ is an isocyanate group, and v is a number from about 1 to about 20, in combination with at least one functionalized polyol.

The biocompatible macromer compositions of the present disclosure may be utilized as adhesives or sealants in a variety of applications, including medical and/or surgical applications. In embodiments, the present disclosure includes methods for closing wounds by applying a biocompatible macromer composition of the present disclosure to a wound and allowing the biocompatible macromer composition to set, thereby closing said wound. Such wounds may include, in embodiments, incisions. Compositions of the present disclosure may also be utilized to fill voids in tissue. In embodiments, compositions of the present disclosure may be utilized to adhere a medical device, such as an implant, to a surface of animal tissue.

DETAILED DESCRIPTION

The present disclosure relates to a macromer composition for use as a tissue adhesive or sealant, which is biocompatible, non-immunogenic and biodegradable. The bioabsorbable macromer composition can be employed to adhere tissue edges, seal air/fluid leaks in tissues, adhere medical devices, i.e. implants, to tissue, and for tissue augmentation such as sealing or filling voids or defects in tissue. The bioabsorbable macromer composition can be applied to living tissue and/or flesh of animals, including humans.

While certain distinctions may be drawn between the usage of the terms "flesh" and "tissue" within the scientific community, the terms are used interchangeably herein as referring to a general substrate upon which those skilled in the art would understand the present bioabsorbable macromer composition to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic and/or ascite tissue.

The composition of the present disclosure includes a diisocyanate-functional polymer possessing bioabsorbable groups, i.e., those which provide degradable linkages. The diisocyanate-functional polymer can be applied by itself or, in embodiments, together with a second component which can be a functionalized triol or polyol, thereby forming a bioabsorbable macromer composition.

The diisocyanate-functional polymer can include polysaccharides and polyols. Suitable polysaccharides include, but are not limited to, sorbitol, mannitol, sucrose, dextran, cyclodextrin, etc. Suitable polyols include, but are not limited to, polyalkylene oxides, polyvinyl alcohols, etc.

In some embodiments, the polymer can be a polyol such as polyethylene glycol ("PEG"), polyethylene oxide ("PEO"), polypropylene oxide ("PPO"), a polyethylene glycol with lactide linkages, polyethylene glycol-adipate, polypropylene glycol ("PPG"), co-polyethylene oxide block or random copolymers, polyethylene glycol-polypropylene glycol copolymers including poloxamers such as polyethylene oxide (PEO) copolymers with polypropylene oxide (PPO) such as the triblock PEO—PPO copolymers commercially available as PLURONICS® from BASF Corporation (Mt. Olive, N.J.), or combinations thereof.

In embodiments a polyalkylene oxide may be utilized as the polymer, such as a polyethylene oxide, such as a polyethylene glycol ("PEG"). As used herein, polyethylene glycol generally refers to a polymer with a molecular weight of less than 50,000, while polyethylene oxide is used for higher molecular weights. PEGs provide excellent water retention, flexibility and viscosity in the biocompatible synthetic macromer composition.

The polymer can have a branched or star configuration for improved biodegradability. The molecular weight of the polymer can be from about 100 to about 20,000, in embodiments from about 500 to about 10,000, typically from about 1000 to about 5000.

Methods for producing the diisocyanate-functional polymer of the present disclosure are within the purview of those skilled in the art. For example, PAOs can be functionalized to have multiple pendant groups according to methods including, for example, those disclosed in Chapter 22 of Poly(ethylene Glycol) Chemistry: Biotechnical and Biomedical Applications, J. Milton Harris, ed., Plenum Press, N.Y. (1992). Various forms of PAOs, in particular PEGs, are commercially available from providers which include, for example, Shearwater Polymers, Inc., Huntsville, Ala., and Texaco Chemical Company Houston, Tex.

In embodiments, the diisocyanate-functional polymer includes bioabsorbable groups. Bioabsorbable groups are known and can include those which undergo hydrolytic degradation. Suitable bioabsorbable groups include hydrolytically labile a-hydroxy acids such as lactic acid and glycolic acid, glycolide, lactide, lactones including E-caprolactone, carbonates such as trimethylene carbonate, ester ethers such as dioxanones including 1,4-dioxane-2-one and 1,3-dioxane-2-one, diacids including succinnic acid, adipic acid, sebacic acid, malonic acid, glutaric acid, azelaic acid, phosphoesters such as ethyl dichlorophosphate, anhydrides such as sebacic acid anhydride and azelaic acid anhydride, etc., and combinations thereof.

Methods for introducing these bioabsorbable groups into diisocyanate-functional polymers are within the purview of those skilled in the art. For example, a bioabsorbable group may be incorporated into a diisocyanate-functional polymer by first reacting the polymer with a polyhydric alcohol such as D-sorbitol, D-mannitol, tris(hydroxymethyl)aminomethane (also known as 2-amino-2-(hydroxymethyl)-1,3-propanediol), enterodiol, cyclodextrins, etc. to form a polymer having multiple hydroxy groups, i.e.,

$$R_1\text{—}(OH)_n \tag{I}$$

where $R_1$ is a member of the group selected from polysaccharides and polyols and n is a number from about 1 to about 20. Suitable polysaccharides include, but are not limited to, sorbitol, mannitol, sucrose, dextran, cyclodextrin, etc. Suitable polyols include, but are not limited to, polyalkylene oxides, polyvinyl alcohols, etc.

The polymer having multiple hydroxy groups may then, in turn, be reacted with a hydroxy acid such as lactic acid or glycolic acid or other bioabsorbable groups as described above to form a polymer having multiple bioabsorbable/hydroxy groups.

The polymer with bioabsorbable groups can then be endcapped with an isocyanate to produce a diisocyanate-functional polymer. Suitable isocyanates for endcapping the polymer with bioabsorbable groups include, but are not limited to, aromatic, aliphatic and alicyclic isocyanates. Examples include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate) or tetramethylxylylene diisocyanate; aliphatic diisocyanates such as tetramethylene diisocyanate, hexamethylene diisocyanate, lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate or commercially available DESMODURS® from Bayer Material Science. An aliphatic diisocyanate, such as hexamethylene diisocyanate, can be particularly useful in some embodiments.

In other embodiments, the polymer can be first endcapped with the diisocyanate groups, and the bioabsorbable group can then be incorporated into the diisocyanate-endcapped polymer.

For example, a low molecular weight crosslinking agent can be combined with a high molecular weight PEG to produce bioabsorbable groups in the diisocyanate-functional bioabsorbable polyalkylene oxide. The crosslinking agent for this embodiment can be diglycolic acid, caprolactone diacid, diacid-terminal oligomers of lactides, glycolides, lactones and combinations thereof, or low molecular weight polypeptides such as poly(glutamic acid). Those skilled in the art will readily envision other reaction schemes for incorporating these components into the endcapped polyalkylene oxide. See, for example, Kobayashi et al., "Water-curable and biodegradable prepolymers," J. Biomed. Materials Res. 25:1481-1494 (1991); Kim et al., "Biodegradable photo linked-cross-linked poly(ether-ester) networks for lubricious coatings," Biomater. 21:259-265 (2000), the entire disclosures of each of which are incorporated by reference herein.

The bioabsorbable groups can be present in the diisocyanate-functional bioabsorbable polymer in amounts from about 5% to about 50% by weight of the diisocyanate-functional bioabsorbable polymer, in embodiments from about 10% to about 40% by weight of the diisocyanate-functional bioabsorbable polymer, typically from about 15% to about 30% by weight of the diisocyanate-functional bioabsorbable polymer.

The diisocyanate-functional bioabsorbable polymer can be linear or can have a branched or star configuration. The molecular weight of the diisocyanate-functional polymer having bioabsorbable groups can be from about 100 to about 20,000, in embodiments from about 300 to about 10,000, typically from about 500 to about 5000.

In some embodiments, the diisocyanate-functional bioabsorbable polymer component can be of the formula

$$R_2\text{-}[A]_v\text{-}R_1\text{-}[A]_v\text{-}R_2 \quad (II)$$

wherein $R_1$ is a polysaccharide or polyol, $R_2$ is an isocyanate group including a diisocyanate group, A is a bioabsorbable group, and v is a number from about 1 to about 20, in embodiments from about 1 to about 6. In an embodiment, $R_1$ may be a polyalkylene oxide such as a polyethylene glycol, and A may be lactide, glycolide, E-caprolactone, trimethylene carbonate, p-dioxanone, anhydrides, phosphoesters, or combinations thereof.

In other embodiments, the diisocyanate-functional polymer can have the following structure:

$$R_2\text{-}[A]_m\text{-}R_3\text{-}[A]_m\text{-}R_2 \quad (III)$$

where A and $R_2$ are as defined above, $R_3$ is a PEG, and m is a number from about 1 to about 6.

In addition to components that provide bioabsorbable groups, at least one linkage that is enzymatically degradable may be incorporated into the diisocyanate-functional polymer. Linkages which are enzymatically degradable include, but are not limited to: an amino acid residue such as -Arg-, -Ala-, -Ala(D)-, -Val-, -Leu-, -Lys-, -Pro-, -Phe-, -Tyr-, -Glu-, and the like; 2-mer to 6-mer oligopeptides such as -Ile-Glu-Gly-Arg-, -Ala-Gly-Pro-Arg-, -Arg-Val-(Arg)$_2$-, -Val-Pro-Arg-, -Gln-Ala-Arg-, -Gln-Gly-Arg-, -Asp-Pro-Arg-, -Gln (Arg)$_2$ -, Phe-Arg-, -(Ala)$_3$-, -(Ala)$_2$-, -Ala-Ala(D)-, -(Ala)$_2$-Pro-Val-, -(Val)$_2$-, -(Ala)$_2$-Leu-, -Gly-Leu-, -Phe-Leu-, -Val-Leu-Lys-, -Gly-Pro-Leu-Gly-Pro-, -(Ala)$_2$-Phe-, -(Ala)$_2$-Tyr-, -(Ala)$_2$-His-, -(Ala)$_2$-Pro-Phe-, -Ala-Gly-Phe-, -Asp-Glu-, -(Glu)$_2$ -, -Ala-Glu-, -Ile-Glu-, -Gly-Phe-Leu-Gly-, -(Arg)$_2$-; D-glucose, N-acetylgalactosamine, N-acetylneuraminic acid, N-acetylglucosamine, N-acetylmannnosamine or the oligosaccharides thereof; oligodeoxyribonucleic acids such as oligodeoxyadenine, oligodeoxyguanine, oligodeoxycytosine, and oligodeoxythymidine; oligoribonucleic acids such as oligoadenine, oligoguanine, oligocytosine, oligouridine, and the like. Those skilled in the art will readily envision reaction schemes for incorporating enzymatically degradable linkages into the diisocyanate-functional polymer.

The diisocyanate-functional polymer component of the present disclosure can be utilized by itself or, in embodiments, combined with a second component to form a macromer adhesive or sealant composition. Where utilized, the second component of the present disclosure can be a functionalized polyol. Useful polyols include polyether-based polyols, polycaprolactone-based polyols, and polyhydric alcohols such as glycerol, trimethylol propane, hexane-1,2, 6-triol, pentaerythritol, glucose, mannitol, disaccharides such as sucrose, sorbitol and diethylene glycol.

Methods for functionalizing these polyols are within the purview of those skilled in the art. In some embodiments, the polyol includes a polycaprolactone-based polyol, such as polycaprolactone triol, functionalized with an isocyanate. Polycaprolactone polyols may be prepared by reacting an excess of a caprolactone with an organic polyfunctional initiator having at least two reactive hydrogen atoms. In some embodiments, a polycaprolactone polyol such as a polycaprolactone triol may be produced by reacting a caprolactone with an initiator such as trimethylol propane, glycerol, diethylene glycol, or combinations thereof.

Useful isocyanates for functionalizing polyols include those noted above for use with the diisocyanate-functional polymer. Examples include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate) or tetramethylxylylene diisocyanate; aliphatic diisocyanates such as tetramethylene diisocyanate, hexamethylene diisocyanate, lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate or commercially available DESMODURS® from Bayer Material Science.

In some embodiments, diisocyanates such as toluene diisocyanate (TDI), 4,4'-diphenylmethane diisocyanate (MDI), 4,4'-oxybis(phenyl isocyanate), 2,4,6-trimethyl-1,3-phenylene diisocyanate)(DESMODURS® ,1,6-hexamethylene diisocyanate (HMDI) and/or isophorone diisocyanate (IPDI) may be utilized to functionalize the polyol.

In embodiments, where polycaprolactone triol is utilized as the polyol, the diisocyanate reacts with the hydroxy groups of the triol to produce the following functionalized polyol:

$$[R_5\text{—}O]_3\text{—}R_4 \quad (IV)$$

wherein $R_5$ is a diisocyanate and $R_4$ is polycaprolactone.

In some embodiments it may be desirable to form an adduct of a diisocyanate with a triol such as trimethylol propane, or a diol such as ethylene glycol or polyethylene glycol, and use this adduct to functionalize the polyol. This can be done by reacting an excess of the diisocyanate with the alcohol to form an isocyanate terminated adduct as exemplified by the following scheme

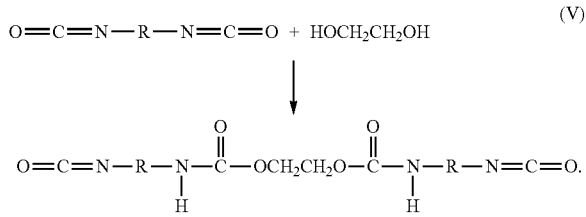

The isocyanate terminated adduct may then be reacted with the polyol, such as a polycaprolactone triol as described above, to produce a polyol functionalized with the adduct. In embodiments, the polyol can be a polycaprolactone triol and the adduct can be polyethylene glycol endcapped with isocyanate groups. One useful functionalized polycaprolactone triol can thus have the following structure:

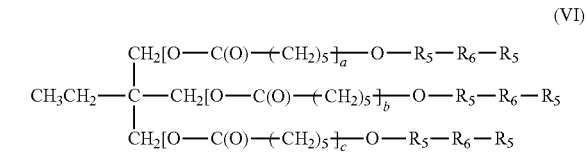

wherein $R_5$ is an isocyanate, including a diisocyanate, $R_6$ is polyethylene glycol, and a, b and c may be any integers, including 0, such that the functionalized polycaprolactone triol has an average molecular weight of from about 200 to about 6,000, in embodiments from about 500 to about 4500.

In other embodiments, the second component can include a polyol which may, in turn, be functionalized with additional hydrolytic groups. These functionalized polyols may, in turn, be endcapped with biocompatible groups such as isocyanates. Suitable polyols include sorbitol, mannitol, disaccharides, cyclodextrins, polyalkylene oxides, and OH-functional dendrimers.

In an embodiment, the polyol includes sorbitol functionalized with bioabsorbable groups noted above as suitable for use with the diisocyanate-functional polymer, i.e., hydrolytically labile a-hydroxy acids including lactic acid and glycolic acid, glycolide, lactide, lactones including E-caprolactone, carbonates such as trimethylene carbonate, ester ethers such as dioxanones including 1,4-dioxane-2-one and 1,3-dioxane-2-one, diacids including succinnic acid, adipic acid, sebacic acid, malonic acid, glutaric acid, azelaic acid, phosphoesters such as ethyl dichlorophosphate, anhydrides such as sebacic acid anhydride and azelaic acid anhydride etc., and combinations thereof.

Such functionalized polyols may be further functionalized with isocyanate groups, so that the second component can have the following structure:

$$R_7—[(R_8)_n—R_9]_d \quad (VII)$$

wherein $R_7$ is the polyol, $R_8$ is the bioabsorbable group, $R_9$ is an isocyanate group including a diisocyanate group, n is a number from about 1 to about 10, and d is a number from about 2 to about 4.

In other embodiments, the polyol of the second component may be further functionalized with a hydrophilic group such as a polyalkylene oxide. In an embodiment, the polyol may be further functionalized with a polyethylene glycol such as methoxy polyethylene glycol ("mPEG") so that the second component possesses the following structure:

$$R_{10}—R_7—[(R_8)_n—R_9]_d \quad (VIII)$$

wherein $R_{10}$ is mPEG, and $R_7$, $R_8$, $R_9$, n and d are as defined above.

In embodiments, $R_{10}$ is mPEG, $R_7$ is sorbitol, $R_8$ is lactide, $R_9$ is an isocyanate, including a diisocyanate, and n is a number from about 1 to about 10 and d is a number from about 2 to about 4.

Thus, in some embodiments the adhesive/sealant composition of the present disclosure can include the diisocyanate-functional polymer with bioabsorbable groups by itself. In other embodiments, the diisocyanate-functional polyalkylene oxide with bioabsorbable groups can be combined with functionalized polyols of formulae IV, VI, VII, or VIII above, or any combinations thereof.

Where utilized, the second component may be present in the macromer composition of the present disclosure in amounts from about 5% to about 90% by weight of the macromer composition, in embodiments from about 10% to about 80% by weight of the macromer composition, typically from about 15% to about 50% by weight of the macromer composition.

The concentrations of the first polymer and the second component will vary depending upon a number of factors, including the types and molecular weights of the particular polymers used and the desired end use application, i.e., as an adhesive or sealant.

Where utilized alone, the diisocyanate-functional polymer with bioabsorbable groups can cross-link in situ to form a biocompatible adhesive or sealant. Where combined with the functionalized polyol, the two components cross-link in situ when mixed together to form a biocompatible macromer adhesive or sealant. The diisocyanate-functional polymer, optionally in combination with the functional polyol, rapidly forms a three dimensional gel-like adhesive matrix, which reduces total surgical/operating time during a medical procedure.

The resulting bioabsorbable macromer compositions can be used in a medical/surgical capacity in place of, or in combination with, sutures, staples, clamps and the like. In embodiments, the bioabsorbable macromer compositions can be used to seal or adhere delicate tissue together, such as lung tissue, in place of conventional tools that may cause mechanical stress. The resulting bioabsorbable macromer compositions can also be used to seal air and/or fluid leaks in tissue as well as to prevent post-surgical adhesions and to fill voids and/or defects in tissue.

The bioabsorbable macromer compositions of the present disclosure can also act as drug carriers, allowing controlled release and direct delivery of a drug to a specific location in an animal, especially a human. As the compositions are synthetic, immuno-reactions in a subject's tissue are reduced or eliminated.

Where the diisocyanate-functional polymer is used alone to form the bioabsorbable macromer composition of the present disclosure, the diisocyanate-functional polymer can be exposed to water, optionally in the presence of a catalyst, to form a bioabsorbable macromer composition of the present disclosure. In embodiments, additional foaming agents may also be added, for example carbonates including sodium bicarbonate, optionally in combination with an organic acid such as citric acid. In other embodiments, initiators may be included. Suitable initiators include, for example, organic peroxides including benzoyl peroxide and azo compounds including azobisisobutyronitrile (AIBN).

In embodiments, the bioabsorbable macromer composition may be prepared by combining the diisocyanate-functional polymer having bioabsorbable groups with the functionalized polyol component to form a three-dimensional crosslinked matrix. Cross-linking is normally performed by exposing the endcapped and functionalized components to water in the presence or absence of a catalyst, such as a tertiary amine catalyst. Suitable catalysts for use in the cross-linking reaction include 1,4-diazobicyclo [2.2.2] octane, triethylamine, diethylaminoethanol, dimethlyamino pyridine, stannous octoate, etc. The amount of catalyst employed can be from about 0.5 grams to about 50 grams per kilogram of the polymer components being cross-linked, in embodiments from about 1 gram to about 10 grams per kilogram of the polymer components being cross-linked.

The exact reaction conditions for achieving cross-linking of the diisocyanate-functional polyalkylene oxide with bioabsorbable groups, optionally in combination with the functionalized polyol, can vary depending on a number of factors such as the composition of the polymer, the degree of endcapping, the specific isocyanate utilized, and the desired degree of cross-linking. The cross-linking reaction may be conducted at temperatures from about 20° C. to about 40° C., in embodiments from about 25° C. to about 35° C., for a period of time from about 5 minutes to about 72 hours or more, in embodiments from about 1 hour to about 36 hours.

For the bioabsorbable macromer composition of the present disclosure, the use of higher concentrations of both the first and second components, i.e., the diisocyanate-functional polymer and functionalized polyol, will result in the formation of a more tightly crosslinked bioabsorbable macromer composition, producing a stiffer and stronger gel matrix. As such, bioabsorbable macromer compositions of the present disclosure intended for use in tissue augmentation will generally use higher concentrations of both the first and second components. Bioabsorbable macromer compositions of the present disclosure intended for use as bioadhesives or for the prevention of post-surgical adhesions need not be as firm and may therefore contain lower concentrations of the two components.

Biologically active agents may be included in the bioabsorbable macromer compositions of the present disclosure. For example, naturally occurring polymers, including proteins such as collagen and derivatives of various naturally occurring polysaccharides such as glycosaminoglycans, can be incorporated into the bioabsorbable macromer compositions of the present disclosure. When these other biologically active agents also contain functional groups, the groups will react with the functional groups on the first and/or second components of the bioabsorbable macromer compositions of the present disclosure.

A variety of optional ingredients including medicinal agents may also be added to the bioabsorbable macromer compositions of the present disclosure. A phospholipid surfactant that provides antibacterial stabilizing properties and helps disperse other materials in the bioabsorbable macromer composition may be added. Additional medicinal agents include antimicrobial agents, colorants, preservatives, or medicinal agents such as, for example, protein and peptide preparations, antipyretic, antiphlogistic and analgesic agents, anti-inflammatory agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, antiulcer agents, hypnotics, antibiotics, antifungal agents, sedative agents, bronchodilator agents, antiviral agents and dysuric agents.

Where the bioabsorbable macromer composition is intended for delivery of a drug or protein, the amounts of the first and second components can be adjusted to promote the initial retention of the drug or polymer in the bioabsorbable macromer composition and its subsequent release. Methods and means for making such adjustments will be readily apparent to those skilled in the art.

Imaging agents such as iodine or barium sulfate, or fluorine, can also be combined with the bioabsorbable macromer compositions of the present disclosure to allow visualization of the surgical area through the use of imaging equipment, including X-ray, MRI, and CAT scan.

Additionally, an enzyme may be added to the bioabsorbable macromer compositions of the present disclosure to increase their rate of degradation. Suitable enzymes include, for example, peptide hydrolases such as elastase, cathepsin G, cathepsin E, cathepsin B, cathepsin H, cathepsin L, trypsin, pepsin, chymotrypsin, y-glutamyltransferase (y-GTP) and the like; sugar chain hydrolases such as phosphorylase, neuraminidase, dextranase, amylase, lysozyme, oligosaccharase and the like; oligonucleotide hydrolases such as alkaline phosphatase, endoribonuclease, endodeoxyribonuclease and the like. In some embodiments, where an enzyme is added, the enzyme may be included in a liposome or microsphere to control the rate of its release, thereby controlling the rate of degradation of the bioabsorbable macromer composition of the present disclosure. Methods for incorporating enzymes into liposomes and/or microspheres are with the purview of those skilled in the art.

The bioabsorbable macromer compositions of the present disclosure can be used for a number of different human and animal medical applications including, but not limited to, wound closure (including surgical incisions and other wounds), adhesives for adhering medical devices (including implants) to tissue, sealants and void fillers, and embolic agents. Adhesives may be used to bind tissue together either as a replacement of, or as a supplement to, sutures, staples, tapes and/or bandages. Use of the disclosed bioabsorbable macromer composition can eliminate or substantially reduce the number of sutures normally required during current practices, and eliminate the subsequent need for removal of staples and certain types of sutures. The disclosed bioabsorbable macromer composition can thus be particularly suitable for use with delicate tissues where sutures, clamps or other conventional tissue closure mechanisms may cause further tissue damage.

Additional applications include use of the bioabsorbable macromer compositions as sealants for sealing tissues to prevent or control blood or other fluid leaks at suture or staple lines. In another embodiment, the bioabsorbable macromer compositions can be used to attach skin grafts and position tissue flaps during reconstructive surgery. In still another embodiment, the bioabsorbable macromer compositions can be used to close tissue flaps in periodontal surgery.

The bioabsorbable macromer composition can be dispensed from a conventional adhesive dispenser, which can provide mixing of the first and second polymers prior to the dispenser. Such dispensers are disclosed, for example, in U.S. Pat. Nos. 4,978,336, 4,361,055, 4,979,942, 4,359,049, 4,874,368, 5,368,563, and 6,527,749, the disclosures of each of which are incorporated by reference herein.

In other embodiments, especially where the bioabsorbable macromer composition of the present disclosure is to be utilized as an implant or a void filler or sealant to fill a defect in an animal's body, it may be advantageous to more precisely control the conditions and extent of cross-linking; thus, it may be desirable to partially cross-link the composition prior to its use to fill a void in animal tissue. In such a case the bioabsorbable macromer composition of the present disclosure can be applied to the void or defect and allowed to set, thereby filling the void or defect.

To effectuate the joining of two tissue edges, the two edges are approximated, and the first component, i.e., the diisocyanate-functional bioabsorbable polymer, is applied alone or in combination with the second component, i.e., a functionalized polyol. The component(s) crosslink rapidly, generally taking less than one minute. It is believed that the isocyanate groups of the component(s) adhere to tissue by linking directly to amine groups present on the tissue surface. In this case the macromer composition of the present disclosure can be used as an adhesive to close a wound, including a surgical incision. The macromer composition of the present disclosure can thus be applied to the wound and allowed to set, thereby closing the wound.

The present disclosure is also directed to a method for using the bioabsorbable macromer composition of the present disclosure to adhere a medical device to tissue. In embodiments, depending on the composition of the medical device, a coating may be required on the medical device. In some cases such a coating can include the first component of the bioabsorbable macromer composition of the present disclosure, or where utilized, the second component. In some aspects, the medical device includes an implant. Other medical devices include, but are not limited to, pacemakers, stents, shunts, and the like. Generally, for adhering a device to the surface of animal tissue, the macromer composition of the present disclosure can be applied to the device, the tissue surface, or both. The device, bioabsorbable macromer composition, and tissue surface are then brought into contact with each other and the bioabsorbable macromer composition is allowed to set, thereby adhering the device and surface to each other.

The present bioabsorbable macromer composition can also be used to prevent post surgical adhesions. In such an application, the bioabsorbable macromer composition is applied and cured as a layer on surfaces of internal tissues in order to prevent the formation of adhesions at a surgical site during the healing process. In addition to the formation of adhesion barriers, the composition of the present disclosure may be utilized to form implants such as gaskets, buttresses, or pledgets for implantation.

When used as a sealant, the bioabsorbable macromer composition of the present disclosure can be used in surgery to prevent or inhibit bleeding or fluid leakage both during and after a surgical procedure. It can also be applied to prevent air leaks associated with pulmonary surgery. The macromer composition may be applied directly to the desired area in at least an amount necessary to seal off any defect in the tissue and seal off any fluid or air movement.

Application of the bioabsorbable macromer composition, whether as an adhesive or sealant, with or without other additives, can be done by any conventional means. These include dripping, brushing, or other direct manipulation of the bioabsorbable macromer composition on the tissue surface, or spraying of the bioabsorbable macromer composition onto the surface. In open surgery, application by hand, forceps or the like is contemplated. In endoscopic surgery, the bioabsorbable macromer composition can be delivered through the cannula of a trocar, and spread at the site by any device known in the art.

The present bioabsorbable macromer composition has a number of advantageous properties. The bioabsorbable macromer compositions of the present disclosure are safe, possess enhanced adherence to tissue, are biodegradable, have enhanced hemostatic potential, have low cost, and are easy to prepare and use. By varying the selection of the polymer components, the strength and elasticity of the bioabsorbable macromer composition can be controlled, as can the gelation time.

The bioabsorbable macromer compositions rapidly form a compliant gel matrix, which insures stationary positioning of tissue edges or implanted medical devices in the desired location and lowers overall required surgical/application time. The bioabsorbable macromer compositions exhibit little or no swelling upon gel matrix formation, and therefore retain the positional integrity of the aligned tissue edges and/or location of a medical device. The bioabsorbable macromer compositions form strong cohesive bonds. They exhibit excellent mechanical performance and strength, while retaining the necessary pliability to adhere living tissue. This strength and pliability allows a degree of movement of tissue without shifting the surgical tissue edge. Additionally, the bioabsorbable macromer compositions are biodegradable, allowing the degradation components to pass safely through the subject's body.

In order that those skilled in the art may be better able to practice the features of the present disclosure described herein, the following examples are provided to illustrate, but not limit, the features of the present disclosure.

EXAMPLE 1

Activation of methoxy-PEGs by condensation with hexamethylene diisocyanate (HMDI). HMDI was added to a solution of mPEG and triethylamine (catalyst) in chloroform (J.T. Baker). The reaction mixture (10% w/v) was heated under reflux for 4-6 hours at 60-65° C. (b.p.=61° C.). The polymer, mPEG-NCO, was isolated by precipitation in petroleum ether/diethyl ether (PE/ether) at a ratio of 1:1. Washing with PE/ether and re-precipitation were repeated 2 times. Final products were dried under vacuum. Yields: >90%. Analysis: nuclear magnetic resonance (NMR), Fourier transform infrared (FTIR), differential scanning calorimetry (DSC).

The starting compounds and their amounts are set forth below:

TABLE 1

| No. | Compound | MW/FW g/mol | Mol | Weight (g) | Mol ratio |
|---|---|---|---|---|---|
| 1. | mPEG1900 (Alfa Aesar, Lot # B12L29; Stock # 41563) | 1900 | 0.1 | 190 | 1 |
| 2. | HMDI (Fluka, Lot # 10317/1-40800) b.p.255° C. | 168.2 | 0.3 | 50.4 | 3 |
| 3. | Triethylamine (Aldrich, Batch #: 06615BA) d = 0.726 g/mL | 101.19 | 0.3 | 30.6 | 3 |

EXAMPLE 2

Condensation of mPEG-OCONH(CH$_2$)$_6$—NCO and D-sorbitol. D-sorbitol was dissolved in N,N-Dimethylformamide (DMF) (with slight heating) and then added drop-wise at room temperature to a solution of mPEG-OCONH(CH$_2$)$_6$NCO (MW=2000 or 5000) and triethylamine dissolved in chloroform, while stirring. The reaction temperature was raised from room temperature to ~60-65° C. and the reaction was allowed to proceed for 6-8 hours. If precipitation occurred, additional DMF was added to redissolve the material. The reaction mixture was concentrated on a ROTAVAPOR® rotary evaporator (BUCHI Labortechnik AG), then precipitated in PE/ether. Final products were dried under vacuum under nitrogen. Yields: >80%. Analysis: NMR, FTIR, DSC. The starting compounds and their amounts are set forth below:

TABLE 2

| No. | Compound | MW/FW g/mol | Mol | Weight (g) | Mol ratio |
|---|---|---|---|---|---|
| 1. | mPEG1900-OCONH(CH$_2$)$_6$—NCO | ~2068 | 0.01 | 35 | 1 |
| 2. | D-Sorbitol | 182 | 0.01 | 3 | 1 |
| 3. | Triethylamine (Aldrich, Batch #: 06615BA) d = 0.726 g/mL | 101.19 | 0.3 | 5.2 | 3 |

EXAMPLE 3

Ring opening polymerization (ROP) of L-lactide in bulk. Methoxy-PEG-OCN (CH$_2$)$_6$NH—CO—NH-D-sorbitol-(OH)$_5$, initiator, and L-lactide were heated up to 135-140° C. under N$_2$. Sn(Oct)$_2$, catalyst, was dissolved in a minimal amount of toluene (~1 mL) and added to the melt. The reaction temperature was ~135-140° C. and the reaction proceeded for 15 hours. The reaction mixture was dissolved in chloroform and then precipitated in petroleum ether/diethyl ether (at a ratio of 1:1). Final product was dried under vacuum. Yields: >60%. Analysis: NMR, FTIR, DSC.

The starting compounds and their amounts are set forth below:

TABLE 3

| No. | Compound | MW/FW g/mol | Mol | Weight (g) | Mol ratio |
|---|---|---|---|---|---|
| 1. | mPEG1900-OCONH($CH_2$)$_6$—NCO-D-sorbitol-(OH)$_5$ | ~2250 | 0.01 | 22.50 | 1 |
| 2. | L-lactide (Purac) | 144 | 0.50 | 72.50 | 50 |
| 3. | Sn(Oct)$_2$ (Aldrich Source 28, 417-2 Batch: 14526LO) | 405 | 0.00011-0.00016 | 0.047-0.066 | 500-700 ppm |

EXAMPLE 4

Condensation of mPEG-OCONH($CH_2$)$_6$NH-D-sorbitol-(polylactide-OH)$_5$ with hexamethylene diisocyanate (HMDI). Methoxy-PEG-OCONH($CH_2$)$_6$NH-D-sorbitol-(polylactide-OH)$_5$ and triethylamine (catalyst) were dissolved in chloroform at room temperature. This solution was gradually added to a stirred solution of HMDI in chloroform at room temperature. The condensation reaction was carried out at reflux temperature under nitrogen for 6 hours. After reduction of the solvent by using, a ROTAVAPOR® rotary evaporator, precipitation in petroleum ether/diethyl ether (at a ratio of 1:1) followed. The final product was dried under vacuum under nitrogen. Yields: >90%. Analysis: NMR, FTIR, DSC.

The starting compounds and their amounts are set forth below:

TABLE 4

| No. | Compound | MW/FW g/mol | Mol | Weight (g) | Mol ratio |
|---|---|---|---|---|---|
| 1. | mPEG1900-OCONH($CH_2$)$_6$—NCO-D-sorbitol-(lactide-OH)$_5$ | ~9425 | 0.005 | 47.13 | 1 |
| 2. | HMDI (Fluka, Lot#10317/1-40880) b.p..255° C. | 168.2 | 0.125 | 21 | 25 |
| 3. | Triethylamine (Aldrich, Batch #: 06615BA) D = 0.726 g/mL | 101.19 | 0.5 | 7.5 | 15 |

EXAMPLE 5

Ring Opening Polymerization of Lactide using Propylene Glycol 25.92 grams of lactide (LA; from Purac) and 2.3 grams of propylene glycol (PG; from JT Baker) were combined in a clean, dry, 250 ml round bottom flask. 0.021 grams of stannous octoate dissolved in a small amount of toluene was added. The reaction mixture was heated to 135-140° C. for 15 to 18 hours with stirring under a static nitrogen atmosphere. The resulting structure, (HO-(LA$_3$)-PG-(LA$_3$)-OH), was confirmed using NMR.

EXAMPLE 6

HMDI was added to a solution of the product of Example 5 (HO-(LA$_3$)-PG-(LA$_3$)-OH) and triethylamine (TEA) in tetrahydrofuran (THF) at room temperature. The reaction mixture was heated to reflux (~65° C.) for four hours and then left overnight at room temperature. The resulting material was added to a solution of PEG 400 in THF.

The starting compounds and their amounts are set forth below:

TABLE 5

| No. | Compound | MW/FW g/mol | Mol | Weight (g) | Mol ratio |
|---|---|---|---|---|---|
| 1. | LA$_3$—PG—LA$_3$ | 940 | 0.01 | 9.4 | 1 |
| 2. | HMDI (Fluka, Lot# 10317/1-40800 b.p. 255° C.) | 168 | 0.022 | 3.7 | 2.2 |
| 3. | Triethylamine (Aldrich, Batch # 06615BA d = 0.726 g/mL) | 107 | 0.0025 | 0.25 | 0.25 |
| 4. | PEG 400 (Aldrich Part #202398-500G Batch: 12712 BB) | 400 | 0.01 | 4.0 | 1 |

The reaction mixture was heated to reflux for four hours. The reaction mixture was concentrated using a ROTAVAPOR® rotary evaporator (BUCHI Labortechnik AG). Precipitation in PE/ether (at a 1:1 ratio) followed, with re-precipitation after re-dissolving in THF.

EXAMPLE 7

A functionalized polyol was prepared as follows. HMDI was added to a

THF solution containing polycaprolactone diol, polycaprolactone triol, and TEA (200-250 ml). The reaction mixture was refluxed for four hours then cooled to room temperature overnight while stirring. The resulting material was added to a PEG 200 solution in THF (200-250 ml) and refluxed for 4 hours. The resulting polyol was isolated by precipitation in PE/ether (at a 1:1 ratio). The yield was 99%. Analysis was by NMR.

The starting compounds and their amounts are set forth below:

TABLE 6

| No. | Compound | MW/FW (g/mol) | Mol | Weight (g) | Mol Ratio |
|---|---|---|---|---|---|
| 1. | Polycaprolactone diol (Aldrich) | 530 | 0.045 | 24 | 0.9 |
| 2. | Polycaprolactone triol (Aldrich) | 300 | 0.005 | 1.5 | 0.1 |
| 3. | HMDI (Fluka, Lot # 10317/1-40800 b.p. 255° C.) | 168 | 0.11 | 18.48 | 2.2 |
| 4. | Triethylamine (Aldrich, Batch #06615BA d = 0.726 g/mL) | 101 | 0.015 | 1.5 | 0.3 |
| 5. | PEG 200 (Aldrich) | 200 | 0.052 | 10.4 | 1.05 |

EXAMPLE 8

25.5 grams of glycolide ("G"), 25.0 grams of caprolactone ("CL"), and 1.67 grams of propylene glycol were added to a clean, dry, 500 ml, 2-neck round bottom vessel. The materials were mixed and dried overnight with nitrogen bubbling. After drying, the materials were placed under static nitrogen and heated to 150° C., with continued mixing. Once the materials reached 150° C., 0.04 grams of stannous octoate was added and the mixture was allowed to react for 24 hours. Samples were obtained and tested via NMR and IR. The mixture was then cooled to 130° C.

Once the mixture had cooled, 274.5 grams of UCON 75-H-450, a polyoxyethylene-polyoxypropylene copolymer (PEO/PPO copolymer; commercially available from Dow Chemical Co., Midland, Mich.), and 0.08 grams of stannous octoate were added. The mixture was allowed to react for 6 hours with continuing mixing. The resulting material, 15.5% poly(glycolide-caprolactone) (50% G+50% CL) +84.5% PEO/PPO copolymer (UCON 75-H-450) (sometimes referred to herein as degradable poly(glycolide-caprolactone)-PEO/PPO copolymer material), was then cooled to 50° C. and transferred into glass jars.

EXAMPLE 9

82.50 grams of the degradable poly(glycolide-caprolactone)-PEO/PPO copolymer material produced in Example 8 above was combined with 85.5 grams of HMDI. The materials were heated to 120° C. and mixed at 100 RPM for 21 hours under static nitrogen. The product was then extracted in petroleum ether as follows. Approximately 100 grams of the product and approximately 300 ml petroleum ether were added to a single neck flask equipped with a condenser. The stirred mixture was heated to reflux temperature and maintained at that temperature for 30 minutes. The mixture was then cooled to room temperature, and the solvent was decanted. This was repeated two more times to ensure extraction of unreacted HMDI. The extracted material, HMDI-functionalized degradable poly(glycolide-caprolactone)-PEO/PPO copolymer material, was then vacuum dried for at least 24 hours at less then 1 torr.

It will be understood that various modifications may be made to the embodiments disclosed herein. Therefore the above description should not be construed as limiting, but merely as exemplifications of typical embodiments. Those skilled in the art will envision other modifications within the scope and spirit of the claims appended hereto.

What is claimed is:

1. A bioabsorbable macromer composition comprising:
   a diisocyanate-functional bioabsorbable polymer of the general formula:

$$R_2\text{-}[A]_v\text{-}R_1\text{-}[A]_v\text{-}R_2 \qquad (II)$$

wherein $R_1$ is a polymer selected from the group consisting of polysaccharides and polyols, A is a bioabsorbable group, $R_2$ is an isocyanate group, and v is a number from 1 to about 20; and
   at least one functionalized polyol selected from the group consisting of polyether polyols, polycaprolactone polyols, and polyhydric alcohols.

2. A bioabsorbable macromer composition as in claim 1, wherein the polyol of the diisocyanate-functional bioabsorbable polymer is selected from the group consisting of polyethylene oxide, polyethylene glycol, polypropylene glycol, polyethylene oxide-polypropylene oxide copolymers, polyethylene glycol-adipate, polyethylene glycol-polypropylene glycol copolymers, and combinations thereof.

3. A bioabsorbable macromer composition as in claim 1, wherein the polyol of the diisocyanate-functional bioabsorbable polymer comprises polyethylene glycol.

4. A bioabsorbable macromer composition as in claim 1, wherein the polysaccharide of the diisocyanate-functional bioabsorbable polymer is selected from the group consisting of sorbitol, mannitol, sucrose, dextran, and cyclodextrin.

5. A bioabsorbable macromer composition as in claim 1, wherein the bioabsorbable group of the diisocyanate-functional bioabsorbable polymer is selected from the group consisting of lactic acid, glycolic acid, glycolide, lactide, ϵ-caprolactone, trimethylene carbonate, 1,4-dioxane-2-one, 1,3-dioxane-2-one, succinnic acid, adipic acid, sebacic acid, malonic acid, glutaric acid, azelaic acid, ethyl dichlorophosphate, sebacic acid anhydride, azelaic acid anhydride, and combinations thereof.

6. A bioabsorbable macromer composition as in claim 1, wherein the bioabsorbable group of the diisocyanate-functional bioabsorbable polymer is selected from the group consisting of lactide, glycolide, ϵ-caprolactone, p-dioxanone, trimethylene carbonate, and combinations thereof.

7. A bioabsorbable macromer composition as in claim 1, wherein v is a number from about 1 to about 6.

8. A bioabsorbable macromer composition as in claim 1, wherein the functionalized polyol is selected from the group consisting of polycaprolactone triol, trimethylol propane, and glycerol.

9. A bioabsorbable macromer composition as in claim 1, wherein the functionalized polyol possesses diisocyanate functional groups.

10. A bioabsorbable macromer composition as in claim 9, wherein the functionalized polyol possesses diisocyanate functional groups selected from the group consisting of toluene diisocyanate, 4,4'-diphenylmethane diisocyanate, 4,4'-oxybis (phenyl isocyanate), 2,4,6-trimethyl-1-,3-phenylene diisocyanate, trimethylhexane diisocyanate, 1,6-hexamethylene diisocyanate and isophorone diisocyanate.

11. A bioabsorbable macromer composition as in claim 1, wherein the functionalized polyol comprises sorbitol functionalized with methoxy polyethylene glycol.

12. A bioabsorbable macromer composition as in claim 1, wherein the functionalized polyol possess bioabsorbable groups selected from the group consisting of lactic acid, glycolic acid, glycolide, lactide, c-caprolactone, trimethylene carbonate, 1,4-dioxane-2-one, 1,3-dioxane-2-one, succinnic acid, adipic acid, sebacic acid, malonic acid, glutaric acid, azelaic acid, ethyl dichlorophosphate, sebacic acid anhydride, azelaic acid anhydride, and combinations thereof.

13. A bioabsorbable macromer composition as in claim 1, wherein the polyol of the functionalized polyol comprises sorbitol, the bioabsorbable group comprises lactide, and the bioabsorbable macromer composition further comprises a component selected from the group consisting of biologically active agents, medicinal agents, and enzymes.

* * * * *